(12) United States Patent
Hersh et al.

(10) Patent No.: US 6,337,320 B1
(45) Date of Patent: *Jan. 8, 2002

(54) REPARATIVES FOR ULTRAVIOLET RADIATION SKIN DAMAGE

(75) Inventors: Theodore Hersh, Atlanta; Michael A. Warshaw, Savannah, both of GA (US)

(73) Assignee: Thione International, Inc., Altanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/728,948

(22) Filed: Oct. 11, 1996

(51) Int. Cl.$^7$ .................. C07K 14/475; A61K 38/18; A61K 7/48
(52) U.S. Cl. .................. 514/18; 514/2; 514/844; 424/40
(58) Field of Search .................. 514/2, 18, 844; 424/401

(56) References Cited

U.S. PATENT DOCUMENTS

| 4,602,039 A | | 7/1986 | Cavazza | 514/561 |
| 4,617,187 A | | 10/1986 | Okuyama et al. | 424/94 |
| 4,929,442 A | * | 5/1990 | Powell | 424/85.2 |
| 5,378,461 A | | 1/1995 | Neigut | 424/94.1 |
| 5,397,770 A | * | 3/1995 | Levin et al. | 514/2 |
| 5,418,253 A | | 5/1995 | Cavazza et al. | 514/547 |
| 5,525,628 A | | 6/1996 | Nicola et al. | 514/562 |
| 5,667,791 A | * | 9/1997 | Hersh et al. | 424/401 |
| 5,840,681 A | * | 11/1998 | Hersh et al. | 514/2 |
| 6,030,950 A | * | 2/2000 | Ohlenschager | 514/18 |

FOREIGN PATENT DOCUMENTS

| DE | 3542309 | * | 6/1987 |
| EP | 0516901 | * | 12/1992 |
| WO | 8900427 | * | 1/1989 |
| WO | 9413265 | * | 6/1994 |

OTHER PUBLICATIONS

Chem. Abstract No. 1992:210827, Hirayama et al. Fragrance J. 20(3) pp 49–52.*
Certified English Translation of Fragrance Journal (1992) vol. 20(3) pp. 49–52 (Japanese).*
Certified English Translation of DE 3542309A1 (German).*

* cited by examiner

*Primary Examiner*—Bennett Celsa
(74) *Attorney, Agent, or Firm*—Malcolm B. Wittenberg

(57) ABSTRACT

A composition of L-glutathione (reduced) and selenium and an epidermal growth factor in a topical carrier and method of using the composition to reduce and repair ultraviolet radiation-induced skin damage, both acute injury (sunburn) and chronic damage (photoaging and cutaneous malignancies).

32 Claims, No Drawings

REPARATIVES FOR ULTRAVIOLET RADIATION SKIN DAMAGE

TECHNICAL FIELD OF THE INVENTION

The present invention deals with the combination of several anti-oxidants, including enzymatic co-factors and thiol compounds, and various tissue and cell growth stimulating factors in appropriate delivery vehicles employed in a topical carrier as a means of both minimizing and ameliorating and also concomitantly repairing free radical damage to the skin from ultraviolet radiation and also stimulating the growth, differentiation and maturation of epidermal cells resulting from environmental and metabolic factors.

BACKGROUND OF THE INVENTION

When cutaneous tissues are exposed to radiation such as solar ultraviolet rays (UVA and UVB radiation), damage to the skin ensues, particularly UVB which results in sunburn and tanning. Chronic UV ray exposure contributes to the skin aging process, the so-called photoaging process and in many cases to the development of cutaneous malignancies. Many common pathological factors exist as the various layers of skin are injured from local release of free radical species, emanating from cellular metabolism and enhanced by environmental UV radiation injury, while the skin is exposed to oxygen in the atmosphere as well as ozone, smog, smoke and other pollutants.

The skin repair processes are common to environmental and dermatologic conditions. Cutaneous tissues so exposed to injury, such as UV radiation with resulting "burns," react so that water molecules contained within cells are altered as are lipids of membranes and of extracellular tissues resulting in the formation of a number of noxious free radicals. This phenomenon on the body has also been called oxidant stress and the free radicals are also known as reactive oxygen species. The latter two are known as the process of lipid peroxidation.

Ultraviolet radiation is responsible for the effects of sunburn and tanning of the skin. Moreover, both short and long wave length ultraviolet light contribute to the skin's photoaging and the development of the various types of skin cancer. Photoaging enhances the chronologic changes of skin, known as chronoaging. Ultraviolet B radiation exerts its most harmful effects when the sun is high on the horizon (high noon hours). In contrast, ultraviolet A radiation is more variable with time of day and time of the year making protection to UVA radiation a year round requirement. Sun care products should protect against both UVA and UVB radiation.

Ultraviolet radiation consists of short wave length, high energy UVB rays (290 NM to 320 NM) and longer wave length, lower energy UVA radiation (320 NM to 400 NM). The former is responsible for the range of sunburn damage from slight erythema to painful burns and blistering. These are acute phase effects. In contrast, UVA radiation penetrates the skin's deeper layers, epidermis and dermis, and is more responsible by its attack on collagen for the so-called premature aging of skin or photoaging. Both UVA and UVB by their creation of free radicals may act synergistically on the pathogenesis of skin cancers. In the laboratory, acute phototoxic reactions using the chemical psoralen and ultraviolet A rays have been used to study dermatologic pathologic responses and concomitant repair processes. Skin reactions, such as acute sunburn, includes redness (erythema) and swelling (edema), with resulting infiltration of the dermal layers by inflammatory cells (polymorphonuclear leukocytes, lymphocytes and macrophages) and pigmentation of the overlying skin by stimulation of melanocytes. Besides the aging process, the chronic UV radiation damage may lead to cutaneous malignancies, particularly squamous and basal cell carcinomas, and in many instances to malignant melanomas.

There is a worldwide epidemic of skin cancer. Announcements say "fry now, pay later." In Australia, Sid Seagull, pictured on the beach, urges and reminds all to play it safe in the sun "Slop! Slip! Slap! Slop on the sunscreen, slip on the shirt and slap on the hat." Although there are some variations among countries, the incidence for the three major skin cancers has risen steadily during this century. Most disturbing are the progressive high mortality rates for malignant melanomas. All three neoplasias are associated with ultraviolet radiation exposure, the culture of sun loving and a tanned skin, the diminishing ozone layer, and complicating environmental pollutants. Since World War II, in the USA and other countries, family incomes have risen with more leisure time available for outdoor activities with faster transportation to exotic tropical areas for more sun exposure. This is coupled with modern scant clothing styles for all ages and genders.

In basal cell carcinomas, epidemiologic studies suggest that exposure to the sun up to age 20 initiates a process of carcinogenesis which manifests itself as a neoplasia many years later, particularly as our generations live longer. Exposure to sunlight induces changes in the DNA of epidermal cells and suppresses the local immune system. Moreover, as we age our ability to repair DNA injury emanating from solar damage is markedly reduced. Basal cell carcinomas with an incidence rising from age 30 and a peak at age 70, develop typically in cutaneous exposed areas with strong evidence of chronic sun damage such as wrinkling, irregular pigmentation, collagenosis, telangiectasias and solar keratoses. Early clinical recognition of these lesions is imperative with subsequent complete surgical extirpation.

Squamous cell carcinoma is the second most common skin cancer with a greater morbidity (case fatality rate is 7 per 1000) due to its more aggressive features. This cancer is also on the rise with its true incidence difficult to calculate due to underreporting as lesions are often excised in doctor's offices. Higher case rates are recorded for Caucasians than for Hispanics, Japanese and African-Americans in various series published in the literature. Cutaneous lesions related to squamous cancers include intraepidermal or invasive keratinocyte dysplasias, including solar keratoses and Bowen's Disease. For squamous cell carcinoma a major constitutional risk factor is skin type, which is clinically graded by the reaction of unprotected skin to strong sunlight. The risk is highest for those individuals least able to tan; however, the incidence in Australia is 70 per 100,000 even in those who "just tan but don't burn." Sunlight is the major environmental carcinogen for these neoplasias, particularly UVB with a wave length range of 290 to 320 NM. Although UVA may also play a role, cumulative UV dose is most important in the etiology of this cancer. Early diagnosis and prompt removal of squamous cell carcinoma is paramount. The Skin Cancer Foundation champions their excellent self examination brochure with "Skin Cancer: if you can spot it, you can stop it!"

Although the incidence of malignant melanoma is certainly lower than the two aforementioned carcinomas, the case fatality rate is much higher for melanoma. The mortality rate from the tumor is rising albeit novel therapeutic modalities. Anatomic distribution of melanomas among white populations is predominantly the trunk in males and the lower extremities in females. A strong hypothesis for etiology of melanoma states that intermittent and intense sun exposure of susceptible (untanned) subjects is more important than total lifetime solar exposure. Proximity of residence to the Equator is another risk factor. In addition, association of high sun exposure during childhood with melanoma is related to a higher appearance of numbers of common melanocytic nevi in the exposed skin. This lesion is regarded as both a marker with an elevated risk and a precursor of melanoma. Freckles in adolescents is another strong yet independent risk factor for melanoma. Intense and intermittent sun exposure leads to greater stimulation of the normal function of melanocytes resulting in their proliferation and an increase in cellular melanin production. This occurs because of an increased synthesis of melanocyte—stimulating hormone receptors, which occurs concomitantly with attempts at repair of DNA damage caused by sun radiation.

In 1996, the Centers for Disease Control and Prevention in Atlanta and the American Academy of Dermatology have launched a rigorous and ample campaign for melanoma/skin cancer detection and prevention. Others have followed with prominent nationwide alerts and advertisements. Although prevention with avoidance of peak sun hour exposure, protective sunscreens and clothing are beneficial, an added therapeutic preventative is the concomitant use of synergistic antioxidants and sun blockers as in the preparations of the present application to combat and reduce free radicals and their putative cutaneous injury generated by ultraviolet radiation.

Investigators such as Burke et al. as noted in U.S. Pat. No. 4,865,840 conducted experiments in rodents to determine whether oral and/or topical selenomethionine supplementation could reduce the incidence of acute and/or chronic damage to the skin. This included sunburn and pigmentation as well as the development of skin cancers, respectively. These controlled studies showed that the concentration of selenium in skin in areas of topical application of the lotion containing selenomethionine were greater than those of the experimental animals given comparable oral doses. The selenium concentration of untreated skin and liver tissue were similar to those of animals receiving the oral selenium compound. There was no evidence of selenium toxicity in any of the experimental animals. The mice treated with selenomethionine had significantly less skin damage by ultraviolet irradiation, as indicated by reduced inflammation and pigmentation and by later onset and lesser incidence of skin cancers.

Selenium has been shown to be an effective inhibitor of skin tumor promotion in rodent skin, but the mechanism is not precisely known. Perhaps the common inciting factor by the carcinogens is the generation of toxic radicals. Selenium, as the co-factor of the enzyme glutathione peroxidase, detoxifies hydrogen peroxide and hydroperoxides within cells. This selenium-glutathione complex may lower the level of potentially damaging peroxide radicals that are generated from various carcinogenic promoting chemicals and radiation energy.

Histopathologically, acute ultraviolet exposure which causes sunburn (so-called solar erythema) is associated with the development of altered epidermal cells becoming dyskeratotic and known as sunburn cells. Likewise, this UV injury has been shown to alter epidermal Langerhans cells which are essential in the cutaneous immune response, by activating helper T lymphocytes. Although accounting for only 2–4% of the epidermal cell populations, Langerhans cells are photodamaged by acute UV rays which results in impaired immune responses locally. Epidermal cells have also been shown to become depleted of their reduced glutathione content and in these studies dermal edema and increases in epidermal ornithine decarboxylase (an enzyme which correlates with epidermal cell damage) were related to the quantity of UV doses applied. Glutathione depletion in both epidermis and dermis was not related to cell leakage but to its consumption in the cell as an antioxidant. L-glutathione locally imparts a prime protective effect on the skin as the solar rays generate free radicals. Topical sunscreens ameliorate but do not prevent sunburn damage. The present invention is based upon the realization that local cutaneous antioxidants will reduce the damage which is caused by the ensuing free radical species.

During the process of phagocytosis by polymorphonuclear leucocytes (PMN), an increased consumption of oxygen occurs. This "respiratory burst" generates superoxide radicals ($O_2^-$), hydrogen peroxide ($H_2O_2$), the hydroxyl radical ($OH^-$) and hypochlorous acid (HOCl). Hydrogen peroxide is derived from the free oxygen species by a process called dismutation while, in the presence of catalytic iron, the hydroxyl radical peroxidizes polyunsaturated fatty acids in cell membranes, which occur in high concentrations in the skin. The ensuing lipid peroxidation decreases membrane fluidity with loss of cellular receptor function. Also, aldehyde derivatives are produced and released which are capable of inhibiting protein synthesis and blocking macrophages.

In skin, oxygen radicals are also made by fibroblasts. Following ultraviolet or thermal burns, there is an increased level of the enzyme xanthine oxidase in the skin, which also generates free oxygen radicals. These free radicals also have effects on gene activation during inflammatory processes in the skin, for they rapidly induce breaks in DNA. These genes encode transcription factors, which play roles in induction of cellular growth, differentiation and development.

The skin is a highly vascular organ, exposed to high levels of atmospheric oxygen and of ultraviolet rays, UVA, UVB and UVC radiation, the latter particularly in ozone depleted zones. The former is essential for the genesis of oxygen free radicals, while the solar radiation is a most potent inducer through UV stimulation of the noxious cellular reactive oxygen species.

Teleologically, the skin's surface has a well developed endogenous oxidant defense system to combat free radicals including the enzymes superoxide dismutase, catalase, selenium dependent glutathione peroxidase and the ubiquitous thiol tripeptide, glutathione, in its reduced form. Also present in the epidermis are the nutritionally provided vitamins C and E, including the hydrophilic antioxidant dehydroascorbate and the lipophilic antioxidant alpha tocopherol, respectively. These two vitamins may also be provided for local use in compositions disclosed herein.

Ultraviolet radiation, particularly UVB, causes acute damage to the skin (sunburn) resulting in a cutaneous inflammatory response. Clinical symptoms include discomfort, pain, tenderness, itching, while local signs include erythema and edema. Skin inflammation associated with itching results in scratching, which further traumatizes the sunburned skin. This trauma causes bleeding into the affected tissues, such that hemoglobin is released from the red blood cells. As aforementioned, when the hemoglobin is exposed to the hydrogen peroxide generated from neutrophils and xanthine oxidase in inflamed tissues, there is hemoglobin degradation and consequent release of catalytic iron ions and toxic free heme and a hemeferryl (iron) species which are themselves capable of initiating lipid peroxidation. These events in sunburned skin aggravate the skin's inflammatory response, the exposed lesions of sunburn skin damage and the consequent excoriations from the pruritus make these sunburns more likely to become infected by secondary bacterial contamination of the wounds.

In addition, cells subjected to oxidative stress may severely affect cellular function and cause damage to membrane lipids, to cytoskeletal structure and to DNA. Free radical damage to DNA has been measured as formation of single-strand breaks, double-strand breaks and chromosomal aberrations. Cells exposed to ionizing radiation and cigarette smoke have also been demonstrated to have an increased intracellular DNA damage. Tissues exposed to radiation result in the breakage of water molecules, with consequent production of the potent hydroxyl radical. This reactive free species sets up a variety of deleterious biochemical chain reactions, including interactions with purine and pyrimidine bases, thereby affecting DNA. Similarly, in clinical conditions which include chronic skin injury due to solar radiation, the aging process, and radiation injury, oxygen free radicals have been shown to be mutagenic and pathogenic of DNA structure and thus DNA changes are related to increased frequency of associated malignancies, including the three types of skin cancer, squamous and basal cell carcinomas and malignant melanoma.

It has been found that sunscreens alone are inadequate in protecting skin from UV radiation and in repairing skin so damaged. There are two types of sunscreens:

1. Reflectants which contain zinc oxide or titanium dioxide;
2. Absorbents, examples of which include P-aminobenzoic acid, benzophenone, methoxycinnamates and salicylates.

Both groups protect against ultraviolet rays A and B radiation depending on the composition of the sunscreen. Evidence shows that sunscreens with high protective factors suppress the development of a premalignant cutaneous lesion called actinic keratoses. Thus, sunscreens may also be useful when used regularly for years in the primary prevention of carcinomas and malignant melanomas. Photo protection is certainly mandatory in those patients who have already experienced one skin tumor in an attempt to prevent a second cutaneous malignancy over sun exposed body surfaces. Although sunscreens protect well against acute sunburn, users should not be lulled into complacency about the amounts of sun exposure they are receiving in order to prevent ultraviolet ray skin damage, creation of free radicals at exposed cutaneous sites, and promotion of dermatologic malignancies. This concern over skin cancers and photoaging has resulted in the use of sunscreen products for daily use including moisturizers and foundation make-up products. These concerns similarly have contributed with the marketing of outdoor UV protectants with high SPF values, many above 15, some above 30 SPF.

The FDA has long ago approved reflectant sunscreen products. Titanium dioxide and zinc oxide are both inorganic chemicals with very little known potential of causing skin irritation or sensitivity to these. However, it becomes more difficult with these inorganics alone to deliver higher SPF values. Moreover, these two must be adequately dispersed within the sunscreen or cosmetic preparations. Other requisites are that the inorganic sunscreens remain dispersed throughout the shelf life of the product and must remain dispersed with the film that is formed on the surface of the body following its application. It has also been shown that sunscreens based solely on inorganics are usually not resistant to wash off following perspiration in the hot outdoors or on contact with water in pools, lakes and seas. Others find that these lack acceptable aesthetic or sensory characteristics. Thus, to achieve higher SPF values, organic active FDA approved sunscreen ingredients are necessary, added to the inorganic formulations or alone as exist in many commercial products. The most common organic ingredient is octyl methoxycinnamate, which has been shown to protect both within the UVB rays and the short UV-A bands. To increase formulations with SPF above 15, it is necessary to use organics with greater absorbency within the UV-A bands of the spectrum. This most commonly used sunscreen is benzophenone-3 (oxybenzone).

In addition to the above, it is hypothesized that when tissues are exposed to radiation, energy is absorbed by water contained within the cells resulting in breakage of the oxygen-hydrogen covalent bonds of the water molecule leaving hydrogen and hydroxyl radicals in situ. It is known that the hydroxyl radical is quite reactive in its interaction with other biomolecules generally thought to be responsible for setting off chain reactions including interactions with the purine and pyrimidine bases of nucleic acids. Many of those who have studied the effects of ultraviolet and gamma radiation on the human body believe that radiation-induced cutaneous carcinogenesis are initiated by free radical damage.

Animals with epithelial tumors have been shown to have increased blood glutathione (GSH) levels. Similarly, higher glutathione levels were detected in groups of humans with disseminated gastric adenocarcinoma and in those with localized or locally advanced skin carcinoma without metastasis. Mean blood GSH levels were 78% and 31% higher, respectively, when compared to control subjects. In blood, most of GSH is present in the red blood cells and may reflect the body's reaction to produce its prime antioxidant, GSH, in response to epithelial malignancies. The rate of generation of GSH within the red blood cells may indicate the body's protective response to reactive species, free radicals, released into plasma by tumors and inflammation.

Antioxidants have been found it all stages of carcinogenesis whereas other antioxidants are more specific and thus more effective against tumor initiation or promotion or tumor progression. Glutathione and selenium have been shown to play prime roles in protection of carcinogenesis, the latter particularly in skin tumors, when selenium is applied locally as selenomethione, selenium yeast extract or other thiol bonds but also in preventing other cancers, when selenium is taken orally thereby replenishing selenium body stores. Likewise, glutathione, the most abundant tissue thiol and antioxidant, inhibits carcinogenesis, as stated, and indeed when its concentration is suppressed by chemicals so that glutathione levels are significantly lowered, chemical carcinogenesis is enhanced and progression of tumor numbers and tumor size increases.

The role of intracellular GSH in irradiated cancer cells has been investigated. Reducing the intracellular levels of GSH in tumor cells increases their sensitivity to irradiation or oxidant damage mediated by activated neutrophils or macrophages. Inhibition of GSH synthesis also augments lysis of murine tumor cells by sulfhydryl-reactive antineoplastics. Thus, neoplastic cells depleted of their endogenous protective antioxidant, GSH, are more sensitive to radiation damage. Conversely, other studies have shown that increases in intracellular GSH are beneficial. An L-cysteine delivery agent not only enhanced endothelial cell GSH concentration, but also protected these cells in an inverse, linear relationship from damage by endogenous hydrogen peroxide. This preventive role of GSH is of value in treating skin which has been exposed to ultraviolet radiation.

It is thus an object of the present invention to provide a composition useful in minimizing early and acute ultraviolet radiation damage, as well as late and chronic radiation induced photo damage which together may enhance or cause photoaging of the skin.

It is yet a further object of the present invention to provide in the form of a topical carrier, certain antioxidants which are effective in reducing ultraviolet radiation-induced cutaneous carcinogenesis which is initiated and promoted by the formation of cutaneous free radicals.

It is yet a further object of the present invention to provide reparative epidermal growth factors to promote skin repair and wound healing from acute sunburn and chronic ultraviolet radiation induced photoaging processes in the skin.

These and further objects will be more readily apparent when considering the following disclosure and appended claims.

SUMMARY OF THE INVENTION

The present invention is directed to a composition and method for reducing the effects of ultraviolet radiation induced skin damage. The composition comprises an effective amount of a glutathione and selenium (as selenoamino acid or selenium yeast extract) as the co-factor of glutathione peroxidase. The combination can be in the form of a lotion, cream, ointment, gel, spray, balm, emulsion and foundation cosmetic preparations and lipsticks and may also include the further endogenous antioxidants acetyl-l-carnitine and superoxide dismutase as well as secondary exogenous components to be discussed hereinafter, plus the epidermal and/or fibroblast growth factors to aid in the tissue repair process by inducing orderly epidermal cell growth and maturation.

DETAILED DESCRIPTION OF THE INVENTION

As previously noted, the present invention deals with reduced L-glutathione (GSH), in combination with selenium and thiol compounds used topically to act as free radical scavengers reducing ultraviolet radiation-induced skin changes. It is proposed that the described active ingredients be employed in topical compositions. Topical carriers are employed which should be both non-irritating to the skin and which are suitable for delivering the active components to the skin. Further, suitable topical carriers should be those which do not inhibit the antioxidant activity of the active ingredients thus reducing the efficiency of the composition for protecting the skin from the effects of acute and chronic ultraviolet radiation. Further, such carriers must be of sufficiently high purity and sufficiently low toxicity to render them suitable for chronic topical administration to the skin and be free of bacterial contaminants.

Certain antioxidants, particularly the endogenous L-glutathione, superoxide dismutase and acetyl L carnitine, as well as the element selenium, a co-factor for the enzyme glutathione peroxidase, and thiol compounds such as L-cysteine, can be employed in suitable carriers such as lotions, solutions, creams, ointments, balms, sprays, aerosols, gels or foundation compositions to protect and to treat the overlying skin surface as a result of the putative acute and chronic UV radiation etiologic factors in specifically dealing with the effects of the various free radicals on biomolecules, lipids, and cell membranes. Moreover, specific cellular growth factors, such as epithelial and fibroblast growth factors in appropriate concentrations and delivery vehicles, are incorporated in the preventive and reparative preparations of this invention for aiding the repair of UV radiation damage of skin and healing of the superficial wounds as occurs in sunburns and in the chronic UV radiation injury known as photoaging of the skin.

Without being bound to any particular theory, it is noted that reduced glutathione is employed in protecting cells and aerobic organisms against oxidative stress by itself being oxidized. Thus, L-glutathione must act in combination with other enzyme systems in order to be reduced so that it may renew its role as a free radical scavenger. GSH functions also coordinately with the enzyme glutathione peroxidase to break down hydrogen peroxide and lipid hydroperoxides. Glutathione peroxidase in the body requires selenium as a cofactor to exert its biologic antioxidant function. Selenium compounds have been shown to scavenge oxygen-centered radicals in vivo with reduced glutathione through glutathione peroxidase. It is believed that selenium-GSH peroxidase catalyzes toxic hydrogen peroxide in the presence of reduced glutathione. This reaction reduces glutathione to oxidized glutathione (GSSG). In turn, the GSSG is reduced back to GSH by the enzyme GSH reductase thereby maintaining abundant cellular GSH to scavenge free radicals anew. GSH reductase is provided in these preparations through thiol rich yeast extracts.

It is further contemplated that the present composition, as a preferred embodiment, includes acetyl L carnitine. This latter component further participates in protecting cells against lipid peroxidation by locally increasing the amount of antioxidizing agents of GSH and ubiquinol. L-carnitine, also known as gamma trimethylamino-beta hydroxy butyrate or Vitamin Bt, occurs naturally in the body. It is a normal endogenous intermediary metabolite which has been identified in all mammalian cells and in blood and urine. It has the function of transporting fatty acids and other acidulated compounds across inner mitochondrial membranes and of maintaining the acyl CoA/free CoA ratio between the mitochondria and the cytosol of the cells. Acetyl L carnitine is the acetyl derivative of l-carnitine and is also a naturally occurring substance in the body as it provides a transport mechanism for the acetyl groups created by the beta oxidation of fatty acids while concomitantly regenerating acetyl co-enzymes in the cytosol of the cell.

Of interest herein, acetyl L carnitine has been shown to have a scavenging effect on the free superoxide anion. This antioxidant activity coupled by acetyl L carnitine's effect of inducing an increase in reduced glutathione and reduced ubiquinone levels provides a stabilizing effect on membranes by decreasing membrane lipid peroxidation.

The skin is a highly vascular organ, extracellularly very rich in polyunsaturated fatty acids. The skin exposed to ultraviolet rays with its exposure to atmospheric oxygen is most prone to the process of lipid peroxidation and thus skin may be readily damaged acutely and/or chronically by this radiation, both UVA and UVB. Thus, reduced glutathione and acetyl L carnitine in a topical preparation will act somewhat synergistically; the former as a reparative antioxidant which itself becomes oxidized and better able to be regenerated locally in its reduced form by the metabolic functions of acetyl L carnitine and by acetyl L carnitine's ability to enhance mitochondrial energy production. This is accomplished by the latter's actions on lipid metabolism and by the resulting increase in cytochrome oxidase, the final enzyme in the cellular respiratory chain.

Further, glutathione and selenium act synergistically in vivo as they are both constituents of the same enzymatic system. GSH serves as a specific donor substrate while selenium, provided from alimentary sources or locally from topically applied preparations of selenoamino acids, selenium yeast extracts or selenoamino acid chelates, provides the prosthetic group of GSH peroxidase, during its synthesis. The glutathione and selenium antioxidant functions are intrinsically related since by keeping a peroxidase in action, the GSH and selenium, contribute to the removal of the dismutation product of free oxygen radicals, namely, hydrogen peroxide. In a broad sense, GSH and selenium modulate free radical chains initiated or sustained by hydro peroxides.

Selenium is used in the present invention for its role as an antioxidant as well as its anticarcinogenic and antimutagenic properties. Selenium is an essential trace element, and a cofactor and constituent of the enzyme glutathione peroxidase. Selenium preparations as a sulfide have been used as topical antiseborrheic detergents (Selsun®) and in veterinary medicine topically for eczemas and dermatomycoses.

Selenomethionine decomposes lipid peroxides and inhibits in vivo lipid peroxidation in tissues of vitamin E deficient chicks. Other selenoproteins also show a high degree of inhibition of lipid peroxidation in hepatic tissues of various species, thus concluding that in vivo selenium exhibits antioxidant behavior.

Selenium has also been shown to affect the immune system. Selenium supplementation as 70% selenomethione in patients with psoriasis with normal pretreatment selenium blood levels showed an increase in blood levels of 40% post treatment, although skin levels of selenium dependent glutathione peroxidase were unchanged in both normal and psoriatic skin. A statistically significant increase in the number of CD4+T-cells was noted in the reticular dermis of the psoriatic lesions.

In other studies in human subjects, optical selenomethionine was investigated for its ability to reduce the degree of acute damage to the skin by sunburn as induced experimentally by ultraviolet irradiation. Eight women were treated for two weeks with a lotion vehicle and then with three concentrations of selenomethionine (0.002%, 0.02% and 0.05%). The researchers found that topical selenomethione was effective in protecting against acute UV damage to the skin, as measured by the minimal erythema dose, using a multiport solar ultraviolet simulator. Plasma levels of selenium in these volunteers remained unchanged, suggesting the protective effect of the selenomethionine was locally at the skin.

The effects demonstrated by topical selenomethinine in human volunteers (Burke et al.) on measurement of minimal erythema dose, suggests that the protection to ultraviolet irradiation by this compound is not simply a sunscreen effect. The selenomethionine is absorbed percutaneously and acts locally as a free radical scavenger, after absorption from the outer skin layers, acting most likely as the co-factor for the enzyme glutathione peroxidase. Thus, even if the person perspires or goes swimming, selenomethionine continues to afford its protective effect as a local antioxidant and not as a sun blocker, which needs to be reapplied to the skin to render its value as a protectant or absorber of UV irradiation. No selenium toxicity is possible at the doses used in these topical compositions (0.001 to 0.05% with an average dose at 0.025%) for studies have indicated selenium toxicities occur in excess of oral 4000 micrograms per day for prolonged periods. Like all sunscreen-sun blocking preparations, the compositions disclosed herein require that the active, synergistic complex, which includes selenoamino acid or selenium yeast extract and reduced glutathione be applied topically by the individual about 30 minutes prior to the expected exposure to solar radiation. Moreover, persons expected to be exposed to solar radiation need to heed the other well known sun safety measures, including coverups with clothing, hats and sunglasses.

Compositions of reduced glutathione in the present invention comprise from about 0.001%, preferably from about 0.1% to 15%, more preferably from about 1% to 5% by weight.

The lower limit of concentration for selenomethionine is selected to achieve a composition in which its amount in the topical preparation provides a therapeutic concentration of the selenoamino acid, no lower than 0.001%. The concentrations to be employed are between 0.001% and 5%, but preferably from 0.01 to 1.0% but most preferably from 0.015 to 0.05% by weight.

"Cell growth stimulating compounds or factors" have been described as natural or exogenous compounds which have a stimulating effect on the elaboration and growth of specific cell lines. These include anabolic growth hormones, as human growth hormone and thyroid stimulating hormone, or on specific cell lines as granulocytes, platelets or erythrocytes. Specifically, in regard to promoting epidermal growth, such as in skin tissue repair or wound healing, various factors have been identified as growth factors, including epithelial (epidermal) growth factor (EGF), fibroblast growth factor (FGF), tissue respiratory factor (TRF), transforming growth factor (TGF) and insulin-like growth factor (IGF).

In the present formulations using antioxidants and anti-inflammatory compounds, one or more cell growth stimulating compounds in suitable amounts effective for stimulating the growth of cells which encompass or surround and are injured or are responsible for healing wounds may be incorporated in the preparation of the present creams, balms, lotions, solutions or gels; patches, sprays or other cosmetic and foundation compositions. Skin cellular reparative functions of dermatologic injuries or lesions (sunburn, gamma radiation and laser burns, chemosurgery, dermatoses, etc.) are included in the list of therapies as examples.

Also useful herein is a component known as tissue respiratory factor (TRF). TRF is a live yeast cell derivative which has been used in over the counter pharmaceutical preparations since the 1940's and more recently as an ingredient in cosmetics. It is commercially available (Brooks Industries Biodynes-TRF™, South Plainfield, N.J.) and purported to be a powerful internal moisturizer which refreshes dry and infirm skin. TRF was first used as an anti-hemorrhoidal product (Preparation H°, Whitehall Laboratories). TRF is composed of low molecular weight glycosidic/peptide fractions, with a ratio of 1:3. The residual glycopeptide linkages are through the amino acid asparagine residues. Because TRF is prepared from live yeast cells derivatives, additional trace quantities of coenzymes, vitamins, amino acids and minerals, characteristic of yeast, are available in these factors, which enhance the therapeutic capabilities of TRF in these pharmaceutic/cosmetic preparations.

TRF has a maximum absorbance of 13.0–20.0; ultraviolet spectrophotometer of a 1% TRF filtered solution reads at 256–258 NM. It is available as a water soluble material for gels, emulsions, lotions and creams. TRF has been shown to promote wound healing through its ability to increase fibroblast synthesis of collagen and elastin fibers resulting in smoothing of the skin. TRF's moisturizing effect is accomplished by increasing uptake of moisture by nascent protein and increasing oxygen utilization in the skin. TRF has been used in the treatment of sunburned skin and has been preferred for decreasing pain and discomfort of sunburn damaged skin when compared to a topical post-sun product containing the local anesthetic benzocaine. Thus, TRF, as other growth factors, may be used in combination to these proposed antioxidant preparations as a preventive and prophylactic agent to photodamaged, burned, irradiated or inflamed skin of diverse etiologies.

A further optional expedient is the use of epidermal growth factor (EGF). Epidermal growth factor is an endogenous substance for the development and maintenance of the epidermis and dermis. EGF is a protein that catalyzes the cutaneous healing process by promoting epidermal and epithelial cells to divide and grow. It induces mitoses, so that skin constantly produces and uses EGF, particularly when skin is damaged, such as in ultraviolet radiation and after surgery, and trauma for both healing and reduction of scar and keloid formation. When applied topically, EGF generates and replaces epithelial cells. EGF also promotes synthesis of proteins, accumulation of collagen and formation of blood vessels. Following sunlight injury and during the aging process, topical application of EGF replaces the existing low levels of dermal growth factors to achieve improvement in the quality of the skin, thereby reducing sagging skin and wrinkles. The antioxidants protect and repair damaged skin from free radicals while the growth factors to be used in combinations will promote epidermal cell renewal and thus ensue in repair of affected tissues, minimizing photodamage and mutations which promote cutaneous carcinogenesis.

Epidermal growth factor is a 53 amino acid polypeptide which stimulates messenger RNA, DNA and protein synthesis. In vitro it stimulates keratinocyte division and in vivo epidermal cell regeneration.

After cutaneous injury, residual epithelial cells proliferate in an organized fashion to regenerate an intact epidermis. Superficial wounds which do not result in total skin loss but retain at least a portion of the dermal layer, heal primarily by this process of epidermal regeneration. Epidermal growth factor induces replacement of cells by inducing mitosis. Many experiments, animal and human studies, have positively shown the beneficial effect of EGF in the process of wound repair. These clinical situations include partial thickness burns, skin graft donor sites, and chronic skin ulcers. It is also of use in healing radiation skin burns, surgical scars and in the repair process of cosmetic surgeries and cutaneous chemical peels.

Thiol rich yeast extracts also provide glutathione peroxidase and the sulphur groups to promote its synthesis and enhance the glutathione pathways. Thiol yeast extracts are used in concentrations ranging from 0.5% to 8%, most typically 3–5% and usually at 3.75 to 4.25% by weight.

As noted previously, the active ingredients described above can be incorporated in any suitable pharmacologically acceptable carrier which is suitable for topical administration to the human skin. As such, the pharmacologically acceptable carrier must be of sufficient purity and have sufficiently low toxicity to render it suitable for administration to a human noting that, typically, the carrier can represent up to 99.99% and typically from at least approximately 80% of the total composition.

Typical compositions for use herein include a wide variety of physical forms. These include, but are not limited to, solutions, lotions, creams, oils, gels, sticks, sprays, ointments, balms, patches and pastes. Generally, such carrier systems can be described as being solutions, creams, emulsions, gels, solids and aerosols.

Solvents are generally employed in the preparation of suitable topical compositions. Such solvents can either be aqueous or organic based and, in either case, the solvent must be capable of having dispersed or dissolved therein the above-described active components while not being irritating to the user. Water is a typical aqueous solvent while suitable organic solvents include propylene glycol, battalion glycol, polyethylene glycol, polypropylene glycol, glycerol, 1,2,4-butanetriol, sorbitol esters, 1,2,6-hexanetriol, ethanol, isopropanol, butanediol and mixtures thereof. Solvents can be included in the overall composition in amounts ranging from 0.1% to 99% and preferably from 2.0% to 75%. It is noted that compositions of the present invention can be produced in the form of an emollient. A wide variety of suitable emollients are known and may be used herein. In this regard, reference is made to U.S. Pat. No. 5,296,500, the disclosure of which is incorporated by reference.

Alternatively, the present composition can be formulated as a lotion containing from about 0.01% to 10% of the above described active ingredients. Further, the product can be formulated from a solution carrier system as a cream. A cream of the present invention would preferably comprise from about 0.1% to 15% and preferably from 1% to 5% of the above described active ingredients. Lotions and creams can be formulated as emulsions as well as solutions.

It is contemplated that as one embodiment, the active ingredients described above be used as a lotion or cream emulsion of the oil-in-water type or as a water-in-oil type, both of which being extremely well known in the cosmetic field. Multi-phase emulsions such as the water-in-oil type is disclosed in U.S. Pat. No. 4,254,105, the disclosure of which is incorporated herein by reference.

It is further contemplated that the active ingredients of the present invention be formulated from a solution carrier system as an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may comprise from 1% to 99% of an emollient plus to about 0.1% to 99% of a thickening agent. Reference is again made to U.S. Pat. No. 5,296,500 and the citations contained therein for a more complete disclosure of the various ointment, cream and lotion formulations for use herein.

It is important to supply locally both glutathione and the synergistic antioxidants to restore epidermal glutathione levels and enhance the reparative antioxidant chain breaking reactions. It becomes imperative to prevent UV ray damage by prophylaxis with skin care (sun protection) products and appropriate clothing, plus the prevention of free radicals and their neutralization by locally applied chain-breaking antioxidant preparations, as proposed in the present application.

EXAMPLE 1

A composition containing the following ingredients was prepared in making a reparative hand and nail formula.

| Ingredients | Percentage by Weight |
| --- | --- |
| water | 57.2394 |
| hydroxyethylcellulose | 0.735 |
| EDTA | 0.084 |
| carbomer ETD 2050 | 0.095 |
| water for carbomer slurry | 6.025 |
| PEG 7 glycerol cocoate | 0.14 |
| canola oil | 12.64 |
| squalane oil | 0.62 |
| cetearyl alcohol ceteareth 20 | 0.21 |
| cetearyl alcohol polysorbate 60 | 0.4 |
| stearic acid | 3.098 |

-continued

| Ingredients | Percentage by Weight |
|---|---|
| cetyl alcohol | 2.246 |
| cetyl ricinolate | 1.788 |
| phenyldimethicone | 0.99 |
| PEG 10 soya sterol | 0.136 |
| sesame oil | 2.22 |
| cocoa butter | 0.831 |
| sodium hydroxymethylglycinate | 0.4 |
| lecithin | 0.02 |
| sodium PCA | 0.25 |
| marine algae | 5.88 |
| sodium hyaluronate | 0.14 |
| peppermint oil | 0.32 |
| sodium lactate | 0.0376 |
| lactic acid | 0.012 |
| honey | 0.34 |
| dex-panthepol (vitamin B5) | 1.037 |
| thiol yeast extract | 0.22 |
| ascorbyl palmitate (with canola oil) | 0.5 |
| pseudo collagen | 0.2 |
| retinyl palmitate & cholecalciferol | 0.25 |
| carrot oil | 0.08 |
| zinc glycopeptide | 0.165 |
| serum albumin | 0.1 |
| sodium hydroxymethylglycinate | 0.121 |
| threonine | 0.03 |
| green tea | 0.06 |
| L-glutathione | 0.03 |
| superoxide dismutase | 0.03 |
| selenomethionine | 0.03 |
| epidermal growth factor | 0.25 |

In preparation, charge vessel with water, disperse EDTA followed by hydroxyethylcellulose and gradually heat to 65 degrees C. Separately disperse carbomer ETD 2050 into water for carbomer slurry and add to heated EDTA and hydroxyethylcellulose and when uniform add PEG 7 glycerol cocoate. Heat canola oil, squalane oil, cetearyl alcohol ceteareth 20, cetearyl alcohol polysorbate 60, stearic acid, cetyl alcohol, cetyl ricinolate, phenyldimethicone, PEG 10 soya sterol, sesame oil and cocoa butter to 75° C. and add to the mixture above mixing or homogenizing for uniformity. Add sodium hydroxymethylglycinate followed by lecithin, slowly cool to 40° C. and add sodium PCA, marine algae, sodium hyaluronate, peppermint oil, sodium lactate, lactic acid, honey, dex-panthenol (vitamin B5) and thiol yeast extract. Continue to cool to 30° C. and add the remaining ingredients, ascorbyl palmitate (with canola oil), pseudocollagen, retinyl palmitate & cholecalciferol,carrot oil, zinc glycopeptide, serum albumin, sodium hydroxymethylglycinate, threonine, green tea, L-glutathione, superoxide dismutase, selenomethionine, epidermal growth factor.

EXAMPLE 2

A composition containing the following ingredients was prepared in making a protein gel masque.

| Ingredients | Percentage by Weight |
|---|---|
| hydroxyethylcellulose | 1.33 |
| water | 77.1 |
| water | 9.5 |
| carbomer | 0.18 |
| PEG 7 glycerol cocoate | 0.15 |
| dex panthenol (vitamin B5) | 0.88 |
| sodium hydroxymethylglycinate | 0.53 |
| zinc glycopeptides | 0.11 |

-continued

| Ingredients | Percentage by Weight |
|---|---|
| marine algae | 3.88 |
| ascorbyl glucosamine | 0.02 |
| sodium PCA | 0.5 |
| serum albumin | 0.6 |
| plant pseudocollagen | 0.7 |
| sodium hyaluronate, hydrolyzed glycosaminoglycans | 1.5 |
| thiol yeast extract | 2.0 |
| lecithin | 0.02 |
| sodium lactate | 0.07 |
| honey | 0.33 |
| green tea | 0.06 |
| L-glutathione | 0.03 |
| superoxide dismutase | 0.03 |
| selenomethionine | 0.03 |
| epidermal growth factor | 0.25 |

In preparation, mix and heat to 50° C. hydroxyethylcellulose and water (77.1%) until gum thickens. Add water (9.5%) and carbomer together until all carbomer is dispersed, then add hydroxyethylcellulose and water mixture. Add sodium hydroxymethylglycinate and cool to 30° C. At 30° C. on slow agitation, add remainder of the ingredients including dex panthenol (vitamin B5) in the order listed above.

EXAMPLE 3

A composition using the following ingredients was prepared to make a sunburn lotion.

| Ingredients | Percentage by Weight |
|---|---|
| water | 70.136 |
| disodium EDTA | .08 |
| hydroxyethylcellulose | 0.74 |
| carbomer ETD 2050 | 0.067 |
| water | 2.801 |
| PEG 7 glycerol cocoate | 0.105 |
| cetyl alcohol | 2.114 |
| glyceryl stearate & PEG 100 stearate | 0.379 |
| stearic acid | 3.209 |
| sesame oil | 1.52 |
| canola oil | 8.65 |
| phenyldimethicone | .094 |
| cocoa butter | 0.56 |
| PEG 10 soya sterol | 0.12 |
| squalane | 0.095 |
| cetyl ricinoleate | 0.12 |
| triethanolamine 99% | 0.305 |
| lecithin | 0.054 |
| sodium hydroxymethylglycinate | 0.07 |
| niacinamide | 0.09 |
| green tea | 0.03 |
| echinacea | 0.047 |
| sodium hyaluronate, hydrolyzed glycosaminoglycans | 0.16 |
| sodium lactate | 0.035 |
| lactic acid | 0.0018 |
| marine algae | 2.13 |
| dex panthenol (vitamin B5) | 0.714 |
| arnica oil | 0.096 |
| calendula oil | 0.096 |
| vitamin C (ascorbyl palmitate) in canola oil | 0.284 |
| honey | 0.29 |
| NaPCA | 0.16 |
| zinc glycopeptide | 0.048 |
| diazolidinyl urea, methyl paraben, propyl paraben | 1.00 |
| carrot oil | 0.0392 |

-continued

| Ingredients | Percentage by Weight |
| --- | --- |
| retinyl palmitate, cholecalciferol | 0.06 |
| selenium yeast extract | 0.11 |
| L-glutathione | 0.03 |
| superoxide dismutase | 0.03 |
| selenomethionine | 0.03 |
| epidermal growth factor | 0.25 |
| micronized titanium dioxide | 3.00 |
| benzophenon, NE3 | .05 |
| fragrance may be added if desired | |

In preparation, mix EDTA into water (70.136%) at 60° C. and then add hydroxyethylcellulose. Add carbomoer ETD 2050 to water (2.801%) and completely dissolve, add to water and hydroxyethylcellulose mixture. Add PEG 7 glycerol cocoate to water mixture. Heat to melt cetyl alcohol, glyceryl stearate & PEG 100 Stearate, stearic acid, sesame oil, canola oil, phenyidimethicone, cocoa butter, PEG 10 soya sterol, squalane and cetyl ricinoleate to a temperature of 65° C., then add to water phase, keeping temperature of water phase at 60° C. during mixing. Add triethanolamine 99% and mix for 5 minutes. Add lecithin and slow mixture down, start cooling to 50° C. and then add sodium hydroxymethylglycinate and niacinamide at a slow mix. Continue to mix slow and bring temperature to 40° C., then add dex-panthenol (vitamin B5). Cool down to 30° C. and add green tea, echinacea, sodium hyaluronate, hydrolyzed glycosaminoglycans, sodium lactate, lactic acid, marine algae. Then add the remainder of the ingredients.

EXAMPLE 4

A composition using the following ingredients was prepared in making a reparative lotion.

| Ingredients | Percentage by Weight |
| --- | --- |
| water | 71.781 |
| disodium EDTA | .08 |
| hydroxyethylcellulose | 0.74 |
| carbomer ETD 2050 | 0.067 |
| water | 3.33 |
| PEG 7 glycerol cocoate | 0.105 |
| cetyl alcohol | 2.114 |
| glyceryl stearate, PEG 100 stearate | 0.379 |
| stearic acid | 3.209 |
| sesame oil | 1.52 |
| canola oil | 8.65 |
| phenyldimethicone | 0.94 |
| cocoa butter | 0.56 |
| PEG 10 soya sterol | 0.12 |
| squalane oil | 0.095 |
| cetyl ricinoleate | 0.12 |
| triethanolamine 99% | 0.305 |
| lecithin | 0.054 |
| sodium hydroxymethylglycinate | 0.07 |
| niacinamide | 0.09 |
| green tea | 0.03 |
| echinacea | 0.047 |
| sodium hyaluronate | 0.16 |
| sodium lactate | 0.035 |
| lactic acid | 0.0018 |
| seaweed | 2.13 |
| dex panthenol (vitamin B5) | 0.714 |
| arnica oil | 0.096 |
| calendula oil | 0.096 |
| ascorbyl palmitate in canola oil | 0.284 |
| honey | 0.29 |
| NaPCA | 0.16 |
| zinc glycopeptide | 0.048 |

-continued

| Ingredients | Percentage by Weight |
| --- | --- |
| diazolidinyl urea, methyl paraben, propyl paraben and propylene glycol | 1.0 |
| carrot oil | 0.0392 |
| retinyl palmitate, cholecalciferol | 0.06 |
| selenium yeast extract | 0.11 |
| L-glutathione | 0.03 |
| vitamin E tocopheryl acetate | 0.03 |
| superoxide dismutase | 0.03 |
| selenomethionine | 0.03 |
| epidermal growth factor | 0.25 |

In preparation, add disodium EDTA to water (71.781%). Add hydroxyethylcellulose to mixture and slowly raise water temperature to 65° C. When hydroxyethylcellulose is dispersed and has thicked, add pre-mixed carbomer ETD 2050 and water (3.33%). Heat PEG 7 glycerol cocoate, cetyl alcohol, glyceryl stearate, PEG 100 Stearate, stearic acid, sesame oil, canola oil, phenyldimethicone, cocoa butter, PEG 10 soya sterol, squalane oil and cetyl ricinoleate to 75° C., add to water phase when water phase is fully dispersed and uniform, mix well for at least 5 to 10 minutes and briefly homogenize if necessary, keeping temperature at 58° to 60° C. during mixing. Add triethanolamine 99% and mix for 5 minutes. Add lecithin and slow mixer down. Start cooling to 50° C. and then add items sodium hydroxymethylglycinate and niacinamide. Mix slowly to 40° C., then add green tea, echinacea, sodium hyaluronate, sodium lactate, lactic acid, seaweed, dex panthenol (vitamin B5), arnica oil, calendula oil, ascorbyl palmitate in canola oil, honey, NaPCA and zinc glycopeptide. Cool to 30° C., then add remainder of ingredients.

EXAMPLE 5

A composition using the following ingredients was prepared in formulating a body lotion.

| Ingredients | Percentage by Weight |
| --- | --- |
| water | 69.67 |
| disodium EDTA | .08 |
| hydroxyethylcellulose | 0.755 |
| carbomer ETD 2050 | 0.072 |
| water | 5.103 |
| PEG 7 glycerol cocoate | 0.12 |
| cetyl alcohol | 2.111 |
| stearic acid | 3.209 |
| sesame oil | 0.52 |
| canola oil | 10.368 |
| phenyldimethicone | 1.031 |
| cocoa butter | 0.561 |
| PEG 10 soya sterol | 0.12 |
| cetyl ricinoleate | 0.2 |
| glyceryl stearate, PEG 100 stearate | 0.379 |
| sodium hydroxymethylglycinate | 0.08 |
| triethanolamine 99% | 0.305 |
| lecithin | 0.054 |
| sodium lactate | 0.036 |
| lactic acid | 0.001 |
| marine algae | 2.343 |
| dex-panthenol (vitamin B5) | 0.5 |
| arnica oil | 0.071 |
| ascorbyl palmitate, canola oil | 0.282 |
| honey | 0.282 |
| NaPCA | 0.233 |
| diazolidinyl urea, methyl paraben, propyl paraben, propylene glycol | 1.01 |
| carrot oil | 0.29 |
| marigold | 0.05 |

| Ingredients | Percentage by Weight |
|---|---|
| zinc glycopeptide | 0.025 |
| L-glutathione | 0.03 |
| green tea | 0.06 |
| superoxide dismutase | 0.03 |
| selenomethionine | 0.03 |
| epidermal growth factor (fragrance may be added if desired) | 0.25 |

In preparation, mix disodium EDTA into water (69.67%), then add hydroxyethylcellulose and heat to 65° C. Add carbomer ETD 2050 and water (5.103%) to totally dissolve, then add to disodium EDTA and hydroxyethylcellulose water phase. Add in PEG 7 glycerol cocoate, keeping temperature at 65° C. Heat to melt cetyl alcohol, stearic acid, sesame oil, canola oil, phenyldimethicone, cocoa butter, PEG 10 soya sterol, cetyl ricinoleate and glyceryl stearate, PEG 100 stearate and add to water phase. Mixwell for at least 5 to 10 minutes, homogenize if needed, keeping temperature at 58° to 60° C. during mixing. Add triethanolamine 99% and mix for 5 minutes, add sodium hydroxymethylglycinate and lecithin and slow the mixer down. Start cooling to 50° C. and add sodium lactate, lactic acid, marine algae, dex panthenol, arnica oil and ascorbyl palmitate, canola oil. Mix slowly to 30° C. and add the remaining ingredients.

EXAMPLE 6

An ointment can be produced according to the following formula.

| Ingredients | Percentage by Weight |
|---|---|
| propylen glycol | .01 |
| vitamin B5 (dex-panthenol) | .01 |
| cholesterol | .028 |
| stearyl alcohol | .029 |
| white wax | .080 |
| white petrolatum | QS |
| superoxide dismutase | .0003 |
| acetyl-l-carnitine HCL | .0003 |
| selenomethionine | .0003 |
| green tea | .00030 |
| epidermal growth factor | .0025 |

EXAMPLE 7

An aerosol formulary concentrate can be produced according to the following formula.

| Ingredients | Percentage by Weight |
|---|---|
| water | .010 |
| vitamin B5 | .010 |
| vitamin C ascorbic acid | .002 |
| glycerin | .010 |
| isopropyl myristate | .011 |
| dipropylene glycol | .051 |
| alcohol | .920 |
| superoxide dismutase | .0003 |
| acetyl-carnitine HCL | .0003 |
| selenomethionine | .0003 |
| green tea | .0060 |
| epidermal growth factor | .0025 |

| Ingredients | Percentage by Weight |
|---|---|
| propellant (60:40) 114/12 | .30 |
| concentrate | .70 |

EXAMPLE 8

A sun gel can be produced according to the following formula.

| Ingredients | Percentage by Weight |
|---|---|
| hydroxyethylcellulose | 1.33 |
| water | 79.275 |
| water | 11.7 |
| carbomer | 0.15 |
| PEG 7 glycerol cocoate | 0.18 |
| dex panthenol (vitamin B5) | 0.88 |
| sodium hydroxymethylglycinate | 0.53 |
| zinc glycopeptides | 0.11 |
| marine algae | 1.00 |
| sodium PCA | 0.5 |
| sodium hyaluronate, hydrolyzed glycosaminoglycans | 1.5 |
| selenium yeast extract | 0.08 |
| lecithin | 0.02 |
| sodium lactate | 0.07 |
| honey | 0.33 |
| green tea | 0.06 |
| L-glutathione | 0.03 |
| superoxide dismutase | 0.03 |
| selenomethionine | 0.03 |
| phynylbenzimidazole sulfonic acid | 2.00 |
| water soluble sunscreen | 0.17 |
| epidermal growth factor | 0.25 |

In preparation, mix and heat to 50° C. hydroxyethylcellulose and water (79.275%) together until gum thickens. Add water (11.7%) and carbomer together until all carbomer is dispersed, then add first water phase. Add sodium hydroxymethylglycinate and cool to 30° C. At 30° C. and on slow agitation, add remainder of the ingredients in the order given.

EXAMPLE 9

A suitable composition for use of the present invention as a reparative cream is as follows:

| Ingredients | Percentage by Weight |
|---|---|
| water | 59.751 |
| hydroxyethylcellulose | 0.8 |
| EDTA | 0.09 |
| glycerol cocoate | 0.14 |
| sesame oil | 8.73 |
| canola oil | 5.98 |
| squalane oil | 0.95 |
| cetearyl alcohol & ceteareth 20 | 0.215 |
| cetearyl alcohol & polysorbate 60 | 0.254 |
| stearic acid | 3.099 |
| cetyl alcohol | 2.348 |
| cetyl ricinoleate | 1.787 |
| phenyldimethicone | 1.062 |
| PEG 10 soya sterol | 0.122 |
| cocoa butter | 0.84 |
| triethanolamine 99% | 0.29 |
| lecithin | 0.02 |

-continued

| Ingredients | Percentage by Weight |
| --- | --- |
| sodium PCA | 0.27 |
| seaweed | 5.54 |
| sodium hyaluronate | 0.193 |
| marigold | 0.2 |
| sodium lactate | 0.038 |
| lactic acid | 0.018 |
| honey | 0.452 |
| vitamin B5 | 1.038 |
| vitamin B complex | 0.215 |
| vitamin C and oil mix | 1.226 |
| pseudo Collagen | 0.93 |
| vitamins A and D3 | 0.7 |
| carrot oil | 0.09 |
| zinc glycopeptide | 0.17 |
| serum albumin | 0.857 |
| Germaben II ® (propyleneglycol, diazolidinyl urea, methyl paraben, propyl paraben) | 1.065 |
| glutathione | 0.03 |
| selenomethionine | 0.03 |
| acetyl L carnitine HCL | 0.03 |
| green tea | 0.06 |
| superoxide dismutase | 0.03 |
| carbomer | 0.09 |
| epidermal growth factor | 0.25 |

As noted from the above, although applicant can employ commercially available selenium containing selenoamino acids such as L-selenomethionine such as those described in U.S. Pat. No. 4,865,840, the disclosure of which is incorporated by reference herein, applicant can also use as its selenium source, a selenium yeast extract. The proposed preparations may be used alone or in combination with essential mineral glycopeptides. These compounds are formulated in the laboratory by feeding the putative metal ions to living yeast cultures by standard microbiologic techniques. The yeast organisms are able to incorporate the minerals as complexes within the cellular glycoproteins.

These complexes are mineral yeast extracts and are commercially available from suppliers such as Brooks Industries, Plainfield, N.J., Pharmachem, South Hackensack, N.J. and Triarco, Patterson, N.J. The mineral-yeast extracts include the following, alone, or in combination with calcium, copper, germanium, iron, manganese, magnesium, selenium, silicon and zinc. These glycopeptides containing one or more of the aforementioned minerals have been shown to possess less toxicity and increased penetration into the skin. Mineral amino acid chelates may also be used and are widely available from commercial suppliers.

The mineral selenium yeast extract, as noted above, is prepared similarly by feeding the selenium to living yeast cultures. Preparations of selenium yeast extract as Se-glycopeptide, are available as clear, low odor, filtered solutions. These have been shown to have moisturizing, toning and skin revitalizing properties. The selenium yeast extract penetrates into the skin and the selenium participates in its usual metabolic activities, including acting as a co-factor for the enzyme glutathione peroxidase. The addition of selenium yeast extract to these topical preparations enhances these as it synergizes with reduced glutathione and other antioxidants.

Yeast extracts with mineral glycopeptides, such as selenium or zinc glycopeptides as well as thiol rich yeast extracts or tissue respiratory factor may be employed in the present preparations. An additional product which can be utilized herein as active ingredients are sulphur rich yeast extract compounds which are also commercially available as, for example, Clariskin, R.I.T.A. Corporation, Woodstock, Ill. This material is extracted from the cytoplasm of eukaryotic cells of saccharomyces cerevisiae. These sulphur rich yeast extracts purportedly aid in the diminution or elimination of dermatologic "brown age spots" by diverting the process of melanogenesis toward the synthesis of lighter colored pigments in the skin. The reduction of brown melanin production is accomplished through the sulphur rich antioxidant, glutathione and the associated enzyme, glutathione reductase. The latter enzyme is present in this yeast depigmenting extract and its intracellular function is to reduce glutathione (GSSG) that has already been oxidized in its role as an antioxidant as reduced glutathione (GSH). This reaction can be shown as

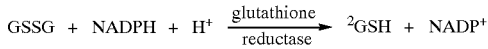

The local relative increase or excess of reduced glutathione (GSH) and other thiol compounds in these cosmetic preparations participate in metabolic reactions by diverting the synthesis of melanocytic pigments, inhibiting the dark pigments (eumelanin) in favor of the biosynthetic pathway toward the clear pigments (pheomelanin). In addition, the glutathione reductase, as aforementioned, participates in the enzymatic reaction toward production of GSH, thus enhancing the anti-free radical activity of these complex and synergistic compounds.

The skin's brown spots are a result of over production of melanin by a specific cell called melanocyte, although these cells tend to decrease in numbers in the mid-third decade of life, research has revealed that they tend to accumulate in body areas exposed to solar radiation hence localized hyperpigmentation of these areas, particularly the face, neck and hands. Repeated exposure to the sun's ultraviolet rays and the inherent aging process of skin cause these "brown age spots" to appear on exposed skin surfaces. This thiol extract thus is ideal for face and hand lotions or creams, adding a therapeutic property to the synergistic antioxidant group. Thus, the present invention promotes and enhances locally the body's and especially the skin's defense mechanisms to free radical species. Glutathione, as GSH, plus the cofactor selenium of the enzyme glutathione peroxidase, plus thiol compounds and glutathione reductase of this yeast extract complete the body's prime antioxidant components, the glutathione cycle. These preparations, plus other key antioxidants and skin repair factors are able to both prevent and chain break free radical reactions in tissues and cells, concomitantly helping repair the skin or heal the wound, created by the various etiologies so enumerated.

As further noted from several of the examples, the present invention further contemplates the use of additional optional expedients, for example, superoxide dismutase (SOD). SOD is a ubiquitous cellular enzyme whose main function is in protecting cells against oxidative stress. Superoxide dismutases are a family of cytosolic metaloenzymes which specifically remove free oxygen radical ($O_2^-$). There are three distinct forms of SOD, namely, CUZN SOD, MN SOD and extracellular SOD (EC-SOD) which is a copper enzyme located on endothelial cell surfaces. The differences in the SODs is in their aminoacid sequences as well as location at their active sites of the transition metals. It is hypothesized that the enzyme SOD, along with glutathione peroxidase and its selenium cofactor are effective preventive antioxidants because they eliminate molecules involved in the initiation of free radical reactions. SOD also protects intracellular reduced glutathione against radical mediated chain oxidation as the combination of SOD and reduced glutathione prevents redox cycling reactions.

It is also contemplated that, as a further optional expedient that the present composition optimally contain from approximately 0.01% to 10% Japanese green tea. Chemically, extracts of Japanese green tea have been analyzed and characterized. Active ingredients include caffeine, theobromine, theophylline and xanthines which, together, have been shown to reduce irritation of the skin, including that caused by various alpha hydroxy acids and other ingredients in cosmetics, thus making green tea an important supplement in topical cosmetic and dermatological preparations. Green tea also contains potent polyphenols, catechin compounds which effectively act as antioxidant agents to scavenge for radicals. The main catechin constituent of green tea is (-)epigallo catechin gallate (EGCG) which has been shown to possess anti-carcinogenic properties, including in experimental animals, as a cancer chemopreventive agent, by reducing too the specific binding to the cell receptor. It has also been shown that EGCG inhibits hydrogen peroxide formation by human leukocytes, the first cell in the inflammatory cellular response to injury. Thus, categorically, EGCG suppresses oxyradical formation in vivo and so is of value to function synergistically as an exogenous antioxidant in these topical preparations with the active ingredients comprised of endogenous antioxidants.

In a preferred embodiment, the compositions of the present may be enhanced by the addition of zinc salts. Zinc may function by its healing properties on wounds, particularly as zinc oxide, and also to render the present preparations odorless, presumably by removing traces of hydrogen sulfide, which could emanate from sulfur groups used in these preparations. Zinc may also be administered as one of the trace metals prepared in yeast extracts as mineral (zinc) glycopeptides.

Compositions preferably comprise from about 0.001% to about 8% of a zinc salt, more preferably from about 0.01% to about 4%, more preferably still from about 0.1% to about 0.5% by weight.

Zinc, the second most abundant trace metal in the human body and present in all living cells and body secretions, was identified as a trace metal by Ravlin in 1869. 25% of total body zinc content is found in the skin mainly as zinc metaloenzymes. For over 3000 years, zinc in the form of zinc oxide or calamine, has been used in the treatment of wounds. Zinc is still used in castor oil or as zinc oxide for treatment of "diaper rash" and in a vast number of zincated bandages, dressings and creams.

It has more recently been shown that zinc metaloenzynmes in the skin have a prominent role in the reconstruction of the wound matrix. Zinc, along with copper is necessary for cross-linking of collagen fibers in the skin repair process. Although zinc probably plays a role in all stages of healing, zinc concentrations increase at the margins of the wound during the formation of granulation tissue, re-epithelialization and normalization periods, whereas cutaneous calcium requirements are greater during hemostasis and inflammation. The concentrations of zinc in the margins of the wound during repair are 15–20% higher than in contiguous intact skin and are provided from zinc in blood. Since zinc thus is of value in the skin healing process as shown in experimental animals and in clinical studies with zinc oxide, the addition of zinc as an ingredient to these preparations will promote the healing of radiation induced skin damage. The form of presentation of the zinc-aqueous gel or paste, cream in amphillic vehicle, lotion or emollient will influence the amount of zinc that is absorbed by the skin and thereby affect the wound's micro-environment.

Like the same tissue and cellular damage produced by ultraviolet radiation, oxidant by-products of normal metabolism cause extensive damage, as stated, to cells, membranes, DNA, proteins and lipids. Anti-oxidants, as endogenous enzymes and scavenger molecules, like GSH, act as defenses against this oxidant damage. Other exogenous molecules such as the ascorbates and tocopherols also assist in these defense mechanisms acting synergistically with glutathione to effect preventive and reparative mechanisms to oxyradical damage.

Vitamins, as those included in these preparations, are naturally derived from dietary fruits and vegetables, particularly ascorbates and caretenoids, but also are sources of tocopherols. Natural and synthetic vitamins may be taken orally as supplements in various foods and beverages or as pharmaceutic preparations of multivitamins and minerals. These cosmeceutical preparations provide these vitamins in sufficient concentrations to exert locally their physiologic and pharmacologic properties.

Vitamin E, particularly in its alpha-tocopherol moiety, has been employed to inhibit oxidation of oils and fats in foods, cosmetic preparations and drugs. Vitamin E is not only an anti-oxidant but also has anti-inflammatory properties. In skin, vitamin E levels are present in dermis and epidermis, but are depleted by malnutrition and by ultraviolet light, thus their importance too in providing these to act in vivo as antioxidants, elevating the UV exposed tissue levels and thereby protecting affected skin cells. Vitamin E moisturizes and enhances skin smoothness. It is soothing and also participates in skin repair and wound healing, such as occurs in photoaging and sunburn.

Cell membranes and plasma lipoproteins contain alpha tocopherol, which is a lipid soluble molecule that functions as a chain breaking (reparative) anti-oxidant. An —OH attached to the hydrophobic structure of tocopherol easily releases its hydrogen atom, so that peroxyl and alkoxyl free radicals generated during lipid peroxidation then may combine with this anti-oxidant instead of with adjacent fatty acid side chains, thereby terminating this chain reaction process of lipid peroxidation. Experimental evidence shows that the tocopherol radical migrates to the membrane surface. It is then reconverted to alpha tocopherol by its reaction with ascorbic acid (vitamin C). Thus vitamins E and C are synergistic and minimize the toxic effects on lipid peroxidation in cell and basement membranes and lipoproteins. Moreover, glutathione and selenium also act synergistically with vitamin E, the former GSH, by regenerating alpha tocopherol from its tocopheroxyl radical form. Also, vitamins C and E, selenium and glutathione, in experimental animals, have been shown to work together as anti-oxidants in inhibiting skin tumor promotion and/or tumor progression.

Ascorbic acid, vitamin C, plays a significant role in skin metabolism and in synthesis of collagen as a co-factor in hydroxylation reactions for the formation and function of collagen. High vitamin C levels not only stimulate collagen but also reverse epidermal thinning and offer skin protection against ultraviolet rays. These properties of vitamin C are enhanced by using acsorbyl glucoseamine where the polyamine complex protects the ascorbic acid, enhancing the antioxidant and anti-collagenase properties of these products. It is thus a more potent collagen synthesis stimulator. It is commercially available from Collaborative Laboratories, East Setauket, N.Y. Preparations with sunscreen properties and concomitant ability to repair collagen have been accomplished with topically administered ascorbic acid and other free radical scavengers such as pycnogenols. These include extracts from grape pips (seeds) and pine bark. An organic proanthocyanidin with ascorbic acid composition is the subject of U.S. Pat. No. 5,470,874 (Nov. 28, 1995) by Sheldon Lerner which is herein incorporated by reference.

Ascorbates can repair oxidizing radicals directly and are therefore characterized as chain-breaking anti-oxidants. Through this mechanism, ascorbic acid and also tocopherols, have also been shown to reduce significantly chemically induced tumor formation in experimental animals.

Vitamin C, a water soluble exogenous small molecule anti-oxidant, is located in aqueous phases of cells while, as noted, vitamin E is in the lipid portion of membranes. Together they protect lipids and lipid structures against peroxidation. Vitamin C repairs the tocoperoxyl radical and permits that molecule to function again as a tocopherol free radical chain-breaking anti-oxidant. The ascorbate free radical produced in this reaction with tocopherol can be removed from the tissues by a dismutation reaction. The dehydroascorbate and the ascorbate radical can then be removed by enzyme systems that use NADH or NADPH as sources of reducing molecules. Thereby, ascorbate is recycled to protect again the process of lipid peroxidation by its synergistic function with vitamin E.

Thus, these topical preparations will, in their preferred form, contain mixtures of vitamins C and E to enhance locally the anti-oxidant activities of the active ingredients, particularly in their function as chain-breaking anti-oxidants in lipid peroxidation.

The present invention also contemplates, as an optional expedient, the inclusion of vitamin A, retinol, which occurs only in animal organisms and is not found in plants. It is usually extracted from liver oils, mainly in its esterified forms but may also be synthesized in the laboratory. The liver converts carotenoids, particularly beta-carotene, into vitamin A. Vitamin A and its derivatives, particularly vitamin A palmitate (retinyl palmitate) may be used in these preparations, more in concentrations from 0.001 to 1% but more preferably from 0.005 to 0.09% by weight. Retinyl palmitate, a common ingredient in cosmetics, like Vitamin A is essential for normal skin, nail and hair development. It increases skin elasticity and promotes thickening of the epidermis and dermis. In experimental animals, vitamin A has been shown to reverse changes of photo damage. An analog of vitamin A, retinoic acid, has also been shown to reverse changes of chronoaging and photoaging in humans.

Beta-carotene, which is pro-vitamin A, is found in many plants and is a nutrition source and the main coloring matter in carrots and egg yolks. B-carotene is used in cosmetics as a coloring agent and also as a source to the body of vitamin A. Carotene, like vitamin A, may be absorbed by the skin. Carotenoids, including beta-carotene, are small molecule dietary and topical anti-oxidants which also may have anticarcinogenic properties and act as defenses against other degenerative diseases. Carrot oil is rich in vitamin A and carotenoids and may be used in these preparations in a concentration between 0.001% and 1% as a source of these molecules. It is a light yellow essential oil derived from seeds of carrots and has no known toxicity. Carrot seed extract, may also be used and is derived from the seed of daucus carota sativa.

A further expedient is the use of dexpanthenol (panthenol, pro-vitamin B5) which is part of the B complex and precursor of pantothenic acid (vitamin B5). Dexpanthenol is a nutritional and topical factor as a source of vitamin B5, which is present in all cells and is a constituent of co-enzyme A. The activated acetates from acetylation reactions (Krebs cycle) are essential in the synthesis or lipids and proteins and the linkages between these two and carbohydrates. Dexpanthenol is used in these preparations for it is a quick and deep penetrating moisturizer and promotes normal skin keratinization. It has been shown to stimulate fibroblast proliferation and also to promote tissue repair and wound healing.

Moisturizers or emollients are skin softeners whether they are in the forms of creams or lotions. Whatever the designation, emollients or moisturizers all perform the same function: these preparations make the skin feel softer and smother and help reduce the roughness, cracking and irritation. Emollients may also help retard the fine wrinkles of aging. Dryness in the outer layer of the skin, the stratum corneum, is due to an insufficient content of water. Moisturizers help prevent cutaneous water losses as these emollients retard evaporation and indeed may impart also hydration to the dermal layers depending on the ingredients, particularly with the addition of super absorbers, like polyvinyl alcohol, which release water content to the dry skin with lower concentration of water, moisturizers thus help maintain a healthy skin.

In accordance with the present invention, as a further preferred embodiment, one or more cell growth stimulating compounds in suitable amounts effective for stimulating the growth of cells which encompass, or surround, and are injured or are responsible for skin repair and for healing of wounds from ultraviolet radiation damage will be incorporated in the present preparations of creams, lotions, gels, ointments, balms or sprays (aerosols).

Thus, sunburn should be treated with the combination of synergistic endogenous and exogenous antioxidants as outlined herein. Local anesthetics such as benzocaine and related caines may be added to ameliorate discomfort and pain, and tissue respiratory factor, which also diminishes sunburn pain and stimulates fibroblast's metabolic functions to deposit collagen. Also, to enhance the healing of skin, the present invention employs epidermal growth factor and/or other cellular growth factors and hormones, which stimulate epithelial cell growth, vital in the epidermis repair process, to accelerate wound healing. In addition, as noted, lipid peroxidation may be started in the lipid rich skin, as evidenced by metabolic products of peroxidation being assayed from both the burned skin as well as from distant organs to the site(s) of solar injury, especially in lung tissue. This is to be expected as cutaneous vascular injury occurs, releasing the enzyme xanthine oxidase which is present in abundant quantities in vascular endothelium. A drop in blood flow resulting in local hypoxia after the burn may trigger the conversion of the enzyme xanthine dehydrogenase to xanthine oxidase with the resulting production of free oxygen radical and hydrogen peroxide. Thus, the importance of providing chain breaking antioxidants locally for amelioration of lipid peroxidation and the concomitant cellular and tissue damage produced by the free radicals of lipid peroxidation.

Some investigators have postulated that the sunburn reaction to ultraviolet radiation in the skin occurs primarily as a result of increased blood flow to the affected dermal tissues. Prostaglandins may play a role in this vascular response to ultraviolet radiation. Certainly the vascular reaction, erythema, is markedly attenuated by use of a variety of non-steroidal anti-inflammatory drugs (NSAIDS) and corticosteroids. Thus, approved products from a list of NSAIDS and/or corticosteroid compounds may be added to the composition of these topical preparations to enhance their therapeutic effectiveness, by including one or more of these anti-inflammatory agents as additives to the antioxidants and other anti-inflammatory compounds recited heroin.

Each and every compound to be incorporated in the topical preparations will be present in an acceptable concentration to be both effective and safe, with minimal, if any, side effects inherent in these widely prescribed and used anti-inflammatory compounds.

We claim:

1. A topical pharmaceutical composition for reducing the effects of ultraviolet radiation induced skin damage comprising as active ingredients an amount of reduced L-glutathione, selenium and epidermal growth factor to reduce ultraviolet radiation induced skin damage in a suitable carrier for topical application.

2. The composition of claim 1 further comprising acetyl L carnitine.

3. The composition of claim 1 further comprising superoxide dismutase.

4. The composition of claim 1 wherein said selenium is provided as a selenium yeast extract.

5. The composition of claim 1 further comprising thiol yeast extract.

6. The composition of claim 1 further comprising from approximately 0.01% to 10.0% by weight Japanese green tea based upon the weight of active ingredients.

7. The composition of claim 1 further comprising from approximately 0.001% to 8.0% by weight based upon the weight of active ingredients of a zinc compound selected from the group consisting of zinc glycopeptide and zinc oxide based upon the weight of the active ingredient.

8. The composition of claim 1 further comprising a member selected from the group consisting of vitamins A, B5, C and E.

9. The composition of claim 8 further comprising ascorbyl glucoseamine, as the vitamin C.

10. The composition of claim 1 further comprising tissue respiratory factor in the form of a live cell derivative of glycosidic peptide fractions of a ratio of 1:3.

11. The composition of claim 8 wherein said composition includes vitamin A in an amount between approximately 0.001% to 1% by weight based upon the weight of active ingredients.

12. The composition of claim 1 wherein said L-glutathione is employed in said composition in an amount between approximately 0.001% to 15% by weight based upon the weight of active ingredients.

13. The composition of claim 1 wherein said selenium is employed in said composition in an amount between approximately 0.001% to 5% by weight based upon the weight of active ingredients.

14. The composition of claim 1 wherein said selenium comprises selenoaminio acid.

15. The composition of claim 1 wherein said selenium comprises L-selenomethionine.

16. The composition of claim 4 wherein said selenium yeast extract further comprises essential mineral glycopeptides.

17. A method for reducing the effects of ultraviolet radiation induced skin damage comprising topically applying active ingredients in a suitable topical carrier to skin damaged by ultraviolet radiation, said active ingredients comprising reduced L-glutathione selenium and epidermal growth factor.

18. The method of claim 17 further comprising acetyl L carnitine.

19. The method of claim 17 further comprising superoxide dismutase.

20. The method of claim 17 wherein said selenium is provided as a selenium yeast extract.

21. The method of claim 17 further comprising thiol yeast extract.

22. The method of claim 17 further comprising from approximately 0.01% to 10.0% by weight Japanese green tea based upon the weight of the active ingredients.

23. The method of claim 17 further comprising from approximately 0.001% to 8.0% by weight of a zinc salt based upon the weight of the active ingredient.

24. The method of claim 17 further comprising a member selected from the group consisting of vitamins A, B5, C and E.

25. The method of claim 24 further comprising ascorbyl glucoseamine, as the vitamin C.

26. The method of claim 17 further comprising tissue respiratory factor in the form of a live cell derivative of glycosidic peptide fractions of a ratio of 1:3.

27. The method of claim 24 wherein said composition includes vitamin A in an amount between approximately 0.001% to 1% by weight based upon the weight of active ingredients.

28. The method of claim 17 wherein said L-glutathione is employed in said composition in an amount between approximately 0.001% to 15% by weight based upon the weight of active ingredients.

29. The method of claim 20 wherein said selenium is employed in said composition in an amount between approximately 0.001% to 5% by weight based upon the weight of active ingredients.

30. The method of claim 17 wherein said selenium comprises selenoaminio acid.

31. The method of claim 17 wherein said selenium comprises L-selenomethionine.

32. The method of claim 20 wherein said selenium yeast extract further comprises essential mineral glycopeptides.

* * * * *